(12) United States Patent
Brereton et al.

(10) Patent No.: US 12,087,409 B2
(45) Date of Patent: Sep. 10, 2024

(54) METHOD AND SYSTEM FOR PREDICTING PROPERTIES OF CHEMICAL STRUCTURES

(71) Applicant: CYCLICA INC., Toronto (CA)

(72) Inventors: Andrew Edward Brereton, Toronto (CA); Sana Alwash, Mississauga (CA); Stephen Scott Mackinnon, Burlington (CA); Joseph Christian Campbell Somody, Toronto (CA); Andreas Windemuth, Belmont, MA (US)

(73) Assignee: Cyclica Inc., Toronto (CA)

( * ) Notice: Subject to any disclaimer, the term of this patent is extended or adjusted under 35 U.S.C. 154(b) by 711 days.

(21) Appl. No.: 17/276,093

(22) PCT Filed: Sep. 13, 2019

(86) PCT No.: PCT/CA2019/051302
§ 371 (c)(1),
(2) Date: Mar. 12, 2021

(87) PCT Pub. No.: WO2020/051714
PCT Pub. Date: Mar. 19, 2020

(65) Prior Publication Data
US 2022/0051759 A1 Feb. 17, 2022

Related U.S. Application Data

(60) Provisional application No. 62/730,913, filed on Sep. 13, 2018.

(51) Int. Cl.
*G16C 20/30* (2019.01)
(52) U.S. Cl.
CPC .................................. *G16C 20/30* (2019.02)
(58) Field of Classification Search
CPC ........ G16C 20/30; G16C 20/10; G16C 20/40; G16C 20/90
See application file for complete search history.

(56) References Cited

U.S. PATENT DOCUMENTS

| 7,400,982 B2 | 7/2008 | Fischer |
| 2003/0069698 A1 | 4/2003 | Uchiyama |

(Continued)

FOREIGN PATENT DOCUMENTS

| JP | 2006/318048 A | 11/2006 |
| JP | 2016/529879 A | 9/2016 |
| WO | 2018/009631 A1 | 1/2018 |

OTHER PUBLICATIONS

Extended European Search Report for related application 19859569.6, mailed May 31, 2022, 8 pages.

(Continued)

*Primary Examiner* — Mohammad K Islam
(74) *Attorney, Agent, or Firm* — Keller Preece PLLC (57) ABSTRACT

A method for predicting a property of a sample molecule involves, for each of a multitude of reference molecules, obtaining a multitude of fingerprints and at least one property, and obtaining the multitude of fingerprints of the sample molecule. The method further involves for each of the multitude of reference molecules, using each of the multitude of fingerprints, calculating distances to the sample molecule, and for each of the multitude of reference molecules, determining a relative predictive dominance, based on the distances to the sample molecule. The method also involves, for each of the multitude of reference molecules, determining a fitness value based on the relative predictive dominance, and predicting the at least one property of the sample molecule based on the at least one property of the multitude of reference molecules and the fitness values obtained for the reference molecules.

16 Claims, 9 Drawing Sheets

(56) References Cited

U.S. PATENT DOCUMENTS

| | | |
|---|---|---|
| 2004/0083060 A1 | 4/2004 | Church |
| 2004/0199334 A1 | 10/2004 | Kovesdi |
| 2014/0038850 A1* | 2/2014 | Fasan ............... C12Q 1/26 506/11 |
| 2014/0156679 A1 | 6/2014 | Tolbert et al. |
| 2023/0154571 A1* | 5/2023 | Terreux ............... G16C 20/40 706/52 |

OTHER PUBLICATIONS

Willett Peter: "Similarity-based data mining in files of two-dimensional chemical structures using fingerprint measures of molecular resemblance", Wiley Interdisciplinary Reviews: Data Mining and Knowledge Discovery, vol. 1, No. 3, Mar. 24, 2011 (Mar. 24, 2011), pp. 241-251, 11 pages.

Willett Peter: "Enhancing the Effectiveness of Ligand-Based Virtual Screening Using Data Fusion", QSAR & Combinatorial Science, vol. 25, No. 12, Dec. 1, 2006 (Dec. 1, 2006), pp. 1143-1152, 10 pages.

Myint et al. "Molecular Fingerprint-Based Artificial Neural Networks QSAR for Ligand Biological Activity Predictions", Molecular Pharmaceutics, vol. 9, No. 10, Aug. 31, 2012 (Aug. 31, 2012), pp. 2912-2923, 12 pages.

Brereton et al. Predicting Drug Properties with Parameter-Free Machine Learning: Pareto-Optimal Embedded Modeling (POEM); ARXIV. ORG, Cornell University Library, 201 Olin Library Cornell University Ithaca, Ny 14853, Feb. 11, 2020 (Feb. 11, 2020), 37 pages.

Urbano-Cuadrado, M., et al., "Description and Application of Similarity-Based Methods for Fast and Simple QSAR Model Development", QSAR Comb. Sci ,Aug. 8, 2007, vol. 27, No. 4, 12 pages.

Kortagere, S., er al., "New Predictive Models for Blood-Brain Barrier Premeability of Drug-Like Molecules", Pharm. Res. Aug. 1, 2008, vol. 25, No. 8, 22 pages.

Luque Ruiz, I., et al., "QSAR Classification and Regression Models for B-Secretase Inhibitors using Relative Distance Matrices", SAR and QSAR in Environmental Research, Mar. 7, 2018, vol. 29, No. 5, 29 pages.

Luque Ruiz, I., "Robust QSAR Prediction Models for Volume Distribution at Steady State in Humans using Relative Distance Measurements", SAR and QSAR in Environmental Research Jul. 25, 2018, vol. 29, No. 7, 22 pages.

Luque Ruiz, I., "Advantages of Relative versus Absolute Data for the Development of Quantitative Structure—Activity Relationship Classification Models", ACS Publications, Oct. 26, 2017, 13 pages.

Office Action as received in JP application 2021-514314 dated Sep. 8, 2023.

* cited by examiner

```
300A
Pseudo-Code for Determining Relative Predictive Dominance

"""
calculate the dominance relationships between all the children in the set
this refers to how much "closer" a child is to the template molecules, according to what numbers of methods
:param vecs: The distances of one molecule from all training cases
:param weights: array of weights for each fingerprint from 0.0-1.0 of how good the fp is
:return: dominance matrix, dominant count, subordinate count
"""

N : Number of molecules in training set
M: Number of fingerprint types dom_matrix[i,j] : an NxN matrix that will contain the dominance scores.
dom[i] : a vector of length N, listing the number of molecules dominated by each molecule i
sub[i] : a vector of length N, listing the number of molecules that dominate each molecule i
dist[k, i] : an MxN matrix of Tanimoto distances between the test molecule and molecule i, using fingerprint k precompute scores from weights
if weights is not None:
    score = [0.5 * weights[k] for k in 0 .. M]
else:
    score = [0.5 for k in 0 .. M]

for i in 0 .. N:
    s = [0, 0, ..., 0] x N
    num_better = [0, 0, ..., 0] x N
    num_worse  = [0, 0, ..., 0] x N
    for k in 0 .. M:
        v = dist[k,i]
        c = 0.5 + sign(dist[k] - v) * score[k]
        s = s + c
        num_better = num_better + (1 where c > 0.75, 0 otherwise)
        num_worse  = num_worse + (1 where c < 0.25, 0 otherwise)
    num_tied = M - (num_better + num_worse)
    dom_check = ((num_better + num_tied) / M) > 0.9
    sub_check = ((num_worse  + num_tied) / M) > 0.9 dom_matrix[i] = s / M
    dom[i] += count(dom_check and not sub_check)
    sub[i] += count(sub_check and not dom_check)
return dom_matrix, dom, sub
```

*FIG. 3A*

300B
Pseudo-Code for Determining Relative Predictive Dominance

```
# calculate the final rankings, based on the dominance matrix/information
fitness[i] : N dimensional vector that will contain the fitness values for i in 0 .. N:
    # the fitness is the sum of the dominance scores for each child
    s = sum(dom_matrix[i])
    # then, weight the score by the number of children dominating it
    # this favors non-dominated children
    fitness[i] = (float(s)) * (dom[i] + 0.05)) / (sub[i] + 0.05)
return fitness

Compute the prediction probabilities

Np : Number of property values (usually 2)

fitness[k,i] : fitness vector for each property value k, as above.

hit = [0, ..., 0] x Np  # compute all property values at once
for i in 0 .. N:
    j = poem.molProp[i] # Value of property for molecule i
    hit[j] += fitness[j][i]
probs = hit / sum(hit)  # Normalize probability

# Predicted value is that with maximum probability in 'probs'
```

600
Performance Summary

| Property | AP Full | AP Test | Traditional | Classifier | Fingerprint |
|---|---|---|---|---|---|
| AMES Toxicity | 0.8562 | 0.8469 | 0.8041 | Gradient Boosting | Pattern |
| Androgen Receptor | 0.8470 | 0.6183 | 0.4874 | Stochastic Gradient Descent | Morgan Rad:2 |
| Blood Brain Barrier | 0.9736 | 0.9655 | 0.9063 | Stochastic Gradient Descent | Pharm Gobbi |
| Caco-2 permeability | 0.8323 | 0.7627 | 0.7562 | Gradient Boosting | Pharm Gobbi |
| Carcinogenic | 0.7074 | 0.6794 | 0.6786 | Random Forest | Layered |
| CYP450 2C9 Inhibitor | 0.7836 | 0.8312 | 0.6607 | Gradient Boosting | Layered |
| CYP450 2C9 Substrate | 0.6766 | 0.7272 | 0.5442 | Ridge | Layered |
| CYP450 2D6 Inhibitor | 0.7512 | 0.7308 | 0.6054 | Gradient Boosting | Pharm Base |
| CYP450 2D6 Substrate | 0.7879 | 0.8325 | 0.6124 | Stochastic Gradient Descent | Pharm Base |
| CYP450 3A4 Inhibitor | 0.6726 | 0.6724 | 0.6107 | Gradient Boosting | Pattern |
| CYP450 3A4 Substrate | 0.6946 | 0.7464 | 0.5960 | Support Vector Machine | Atom Pair |
| Estrogen Receptor alpha | 0.9570 | 0.9492 | 0.8430 | Gradient Boosting | Pharm Base |
| Human Intestinal Absorption | 0.9533 | 0.9273 | 0.7900 | Ridge | Layered |
| Human Oral Bioavailability | 0.7708 | 0.7875 | 0.6931 | Gradient Boosting | Pharm Base |
| Human Pregnane X Receptor | 0.8864 | 0.8694 | 0.6329 | Ridge | Daylight |
| P-glycoprotein Inhibitor | 0.9458 | 0.9195 | 0.8487 | Gradient Boosting | Pharm Gobbi |
| P-glycoprotein Recognition | 0.9368 | 0.9088 | 0.8019 | Gradient Boosting | Pattern |

METHOD AND SYSTEM FOR PREDICTING PROPERTIES OF CHEMICAL STRUCTURES

CROSS REFERENCE TO RELATED APPLICATIONS

This application is a national phase application of International Application No. PCT/CA2019/051302, which filed on Sep. 13, 2019. International Application No. PCT/CA2019/051302 claims priority to U.S. Provisional Patent Application No. 62/730,913, filed on Sep. 13, 2018, the entire disclosure of which is hereby expressly incorporated by reference herein.

BACKGROUND

Relationships between chemical structures and the activities or properties of these chemical structures are known and documented for many chemical structures. Newly discovered or synthesized sample chemical structures may have initially unknown properties. The similarity of a sample chemical structure to known chemical structures may be used to predict properties of the sample chemical structure.

SUMMARY

In general, in one aspect, one or more embodiments relate to a method for predicting a property of a sample molecule, the method comprising: for each of a plurality of reference molecules, obtaining a plurality of fingerprints and at least one property; obtaining the plurality of fingerprints of the sample molecule; for each of the plurality of reference molecules, using each of the plurality of fingerprints, calculating distances to the sample molecule; for each of the plurality reference molecules, determining a relative predictive dominance, based on the distances to the sample molecule; for each of the plurality of reference molecules, determining a fitness value based on the relative predictive dominance; and predicting the at least one property of the sample molecule based on the at least one property of the plurality of reference molecules and the fitness values obtained for the reference molecules.

In general, in one aspect, one or more embodiments relate to a system for predicting a property of a sample molecule, the system comprising: a reference molecule repository; and a molecule property prediction engine configured to: for each of a plurality of reference molecules, obtaining a plurality of fingerprints and at least one property from the reference molecule repository; obtaining the plurality of fingerprints of the sample molecule; for each of the plurality of reference molecules, using each of the plurality of fingerprints, calculating distances to the sample molecule; for each of the plurality reference molecules, determining a relative predictive dominance, based on the distances to the sample molecule; for each of the plurality of reference molecules, determining a fitness value based on the relative predictive dominance; and predicting the at least one property of the sample molecule based on the at least one property of the plurality of reference molecules and the fitness values obtained for the reference molecules.

In general, in one aspect, one or more embodiments relate to a non-transitory computer readable medium comprising computer readable program code for predicting a property of a sample molecule, the computer readable program code causing a computer system to: for each of a plurality of reference molecules, obtaining a plurality of fingerprints and at least one property; obtaining the plurality of fingerprints of the sample molecule; for each of the plurality of reference molecules, using each of the plurality of fingerprints, calculating distances to the sample molecule; for each of the plurality reference molecules, determining a relative predictive dominance, based on the distances to the sample molecule; for each of the plurality of reference molecules, determining a fitness value based on the relative predictive dominance; and predicting the at least one property of the sample molecule based on the at least one property of the plurality of reference molecules and the fitness values obtained for the reference molecules.

Other aspects of the disclosure will be apparent from the following description and the appended claims.

BRIEF DESCRIPTION OF DRAWINGS

The present embodiments are illustrated by way of example and are not intended to be limited by the figures of the accompanying drawings.

FIG. 3A and FIG. 3B show pseudo-code, in accordance with one or more embodiments of the invention.

DETAILED DESCRIPTION

Specific embodiments disclosed herein will now be described in detail with reference to the accompanying figures. Like elements in the various figures may be denoted by like reference numerals and/or like names for consistency.

The following detailed description is merely exemplary in nature, and is not intended to limit the embodiments disclosed herein or the application and uses of embodiments disclosed herein. Furthermore, there is no intention to be bound by any expressed or implied theory presented in the preceding technical field, background, brief summary or the following detailed description.

In the following detailed description of some embodiments disclosed herein, numerous specific details are set forth in order to provide a more thorough understanding of the various embodiments disclosed herein. However, it will be apparent to one of ordinary skill in the art that the embodiments may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as by the use of the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

In one or more embodiments of the invention, properties of a sample chemical structure are predicted based on known properties of other chemical structures. The method may be used to predict properties of small molecules, i.e., molecules with a low molecular weight. These molecules may be, for example, pharmacological molecules. To assess whether a molecule is pharmacologically useful, its properties may need to be determined. For example, it may be necessary to assess the molecule's distribution, metabolism, excretion and toxicity (ADMET) properties.

Relationships between chemical structures and the activities or properties of these chemical structures are known and documented for many chemical structures. Newly discovered or synthesized sample chemical structures may have initially unknown properties. The similarity of a sample chemical structure to known chemical structures may be used to predict properties of the sample chemical structure. In one or more embodiments of the invention, the quantitative structure-activity relationship (QSAR) is used to make predictions. The subsequently described approach, in accordance with one or more embodiments of the invention, relies on multiple/many reference molecules, each of which may be represented by multiple fingerprints, to make a prediction for a sample molecule.

Figure 1:
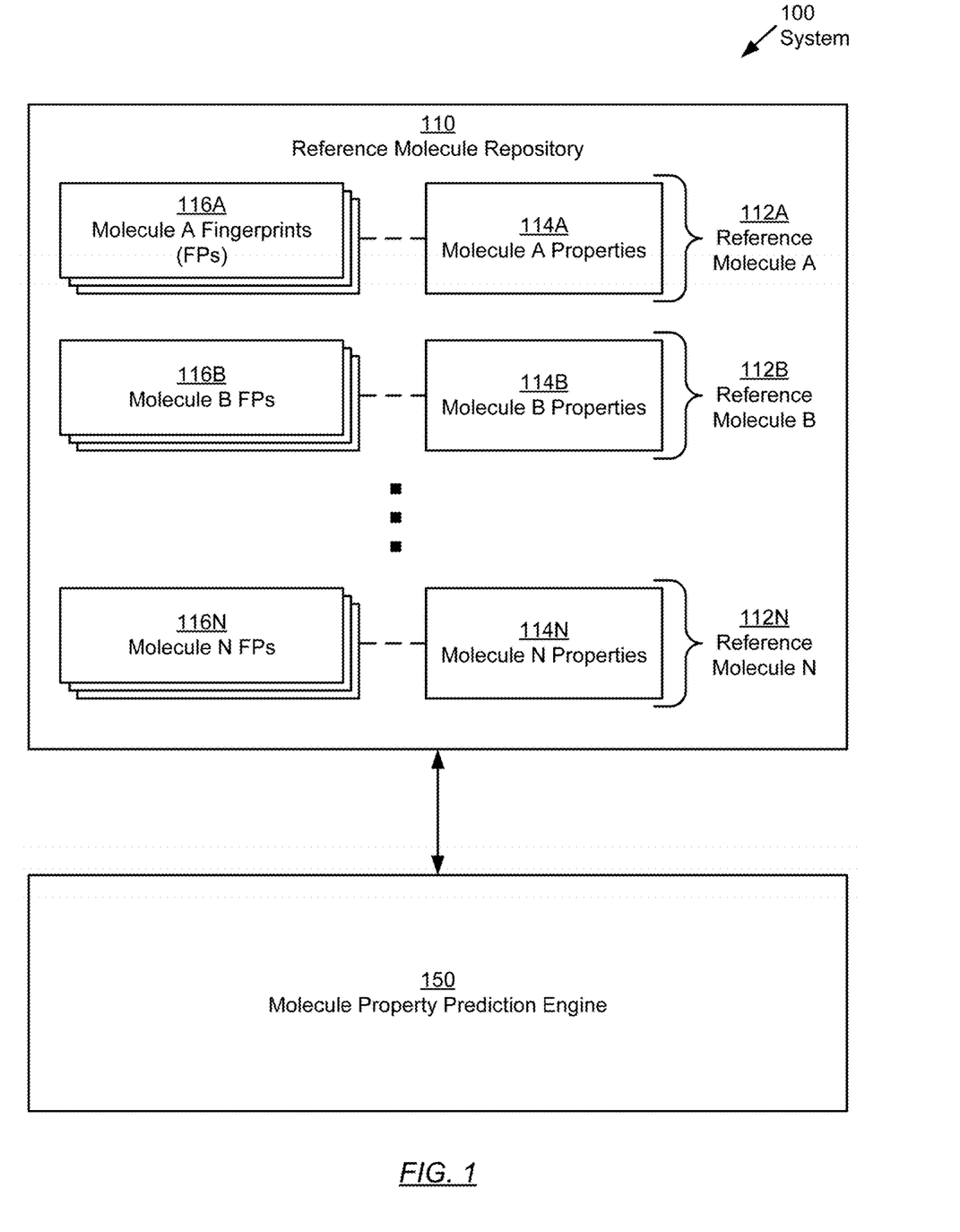
FIG. 1 shows a block diagram of a system in accordance with one or more embodiments of the invention.

FIG. 1 shows a system (100) for predicting properties of chemical structures, in accordance with one or more embodiments of the invention. The system (100) includes a reference molecule repository (110) and a molecule property prediction engine (150). These components are subsequently described.

The reference molecule repository (110) may be any type of storage unit and/or device (e.g., a file system, database, collection of tables, or any other storage mechanism) for storing data. The reference molecule repository (110), in accordance with one or more embodiments of the invention, stores data associated with reference molecules (112A-112N). More specifically, for each reference molecule, molecule fingerprints and molecule properties are stored. Because molecule fingerprints and molecule properties are known, these reference molecules may be used to predict molecule properties of a sample molecule for which only the molecule fingerprints but not the molecule properties are known. Data for any number of reference molecules may be stored in the reference molecule repository (110).

The data stored for the reference molecules (112A-112N), in accordance with one or more embodiments of the invention, include molecule fingerprints (116A-116N) and molecule properties (114A-114N).

Any number of molecule properties may be documented for a molecule. Molecule properties may include, but are not limited to, physicochemical properties, ADMET properties, and biological activity. Examples for ADMET properties are: AMES toxicity, androgen receptor binding, blood brain barrier compatibility, Caco-2 permeability, hERG inhibition, and carcinogenicity.

A fingerprint (or other descriptors), in accordance with one or more embodiments of the invention, captures the structure of the molecule in a descriptor format. A fingerprint is not necessarily unique to one molecule but may allow the underlying molecule to be compared to other molecules to assess the similarity of these molecules. A fingerprint may be, for example, a daylight (standard), atom_pair (standard), morgan2 (morgan with r=2), morgan4 (r=4), morgan2_feat (r=2 and use features), morgan4_feat (etc), pharm_base (pharm with default rdkit factory), pharm_gobbi (pharm with gobbi factory), layered (standard), pattern (standard) fingerprint. A fingerprint may be derived from a SMILES representation of the underlying molecule.

Each type of fingerprint, associated with a molecule, may represent the underlying information (i.e. the molecule itself) in a slightly different way. Each type of fingerprint may, thus, establish an imperfect representation of the underlying molecule with a slightly different noise characteristic.

Continuing with the discussion of FIG. 1, the reference molecule repository (110) is operatively connected to the molecule property prediction engine (150). The molecule property prediction engine (150) includes instructions in the form of computer readable program code to perform at least one of the steps described in FIG. 2.

Figure 2:
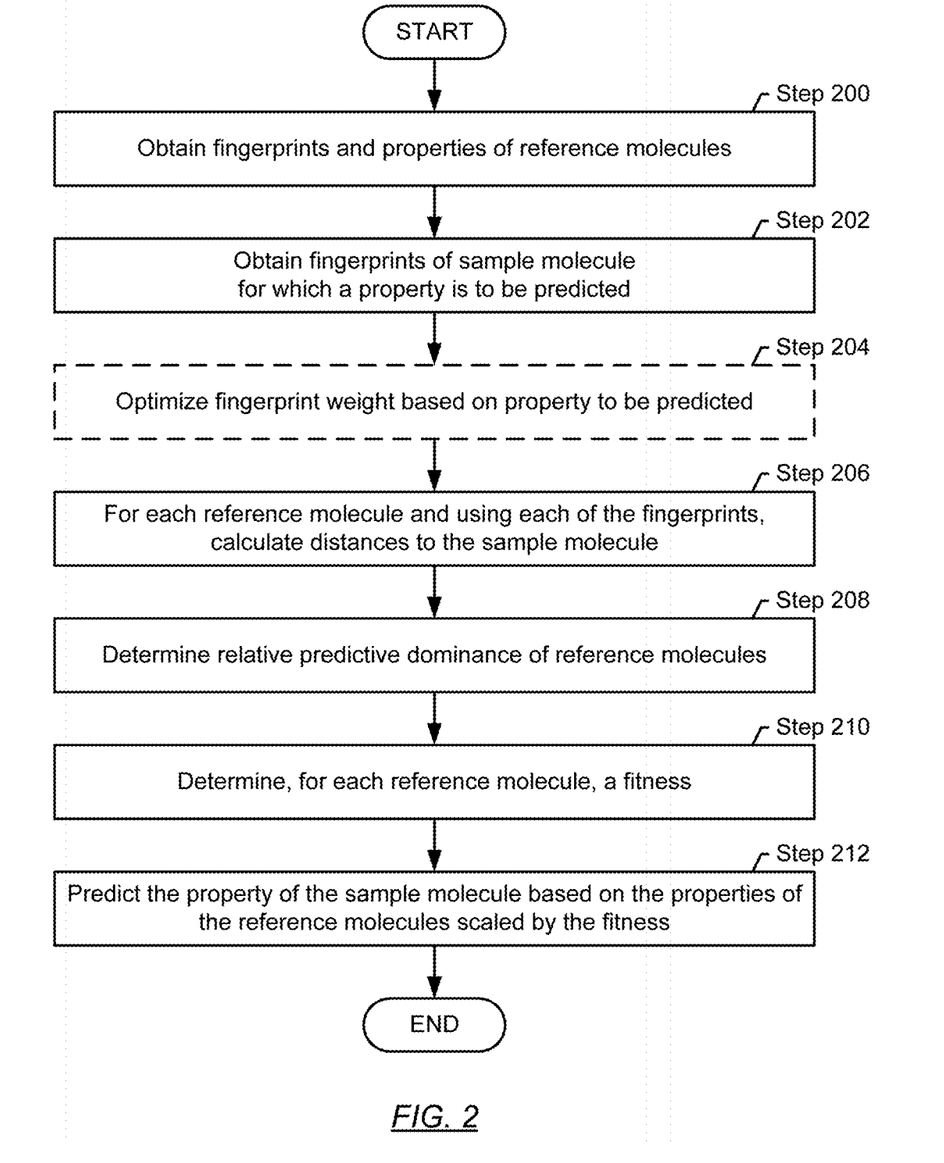
FIG. 2 shows a flowchart, in accordance with one or more embodiments of the invention.

FIG. 2 shows a flowchart in accordance with one or more embodiments. The flowchart of FIG. 2 depicts a method for predicting properties of chemical structures such as small molecules. One or more of the steps in FIG. 2 may be performed by the components of the system (100), discussed above in reference to FIG. 1. In one or more embodiments, one or more of the steps shown in FIG. 2 may be omitted, repeated, and/or performed in a different order than the order shown in FIG. 2. Additional steps may further be performed. Accordingly, the scope of the invention should not be considered limited to the specific arrangement of steps shown in FIG. 2.

In Step 200, fingerprints and properties are obtained for the reference molecules. In one or more embodiments of the invention, multiple fingerprints (for example 10 fingerprints) are obtained for each reference molecule. Each obtained fingerprint may be of a different type. Accordingly, while the underlying information (i.e. the molecule itself), captured by the multiple fingerprints is always the same, it may be captured to a different degree, by the different types of fingerprints. The same types of fingerprints are obtained for each of the reference molecules. Depending on the analysis to be performed, one or more properties may be obtained for each of the reference molecule. For example, if the entire analysis is intended to determine whether a sample molecule is capable of crossing the blood brain barrier (BBB), the BBB crossing property may be obtained for each of the reference molecules. Multiple properties may be obtained if multiple properties are to be assessed.

In Step 202, fingerprints are obtained for the sample molecule. The same types of fingerprints as those obtained for the reference molecules are obtained.

In Step 204, weights for the types of fingerprints may be determined based on the property to be predicted. Broadly speaking, one type of fingerprint may be better at predicting a particular property than other types of fingerprints. Accordingly, a higher weight may be assigned to this type of fingerprint for the subsequent operations. Weights of fingerprints may be determined as follows.

Consider, for example, the capability of a molecule to cross the blood brain barrier (BBB) (BBB crossing property). For each of the reference molecules, the BBB crossing property is assumed to be known. Further, based on the fingerprints of these reference molecules, distances may be calculated from each molecule to each other molecule. Accordingly, for each possible pair of reference molecules and using all available fingerprints, distances may be calculated. To determine the weights, correlations of distances between molecules based on the fingerprints, and the BBB crossing property may be analyzed. Generally speaking, one may expect that for a pair of reference molecules, fingerprints that are closer are more likely to represent similar BBB crossing properties than fingerprints that are more remote. A fingerprint with a short distance between two reference molecules that have identical BBB crossing properties (i.e., both reference molecules being able to pass the blood brain barrier (BBB++) or both molecules failing to pass the blood brain barrier (BBB−−)) may therefore be assigned a high weight. When this analysis is performed for many molecules (e.g., for all reference molecules), one may probabilistically assess the fingerprint's ability to predict BBB crossing properties. A fingerprint that is associated with high probabilities for matching properties, P(BBB−−) and P(BBB++), is assigned a high weight, whereas a fingerprint that is associated with lower probabilities for matching characteristics, P(BBB−−) and P(BBB++) (thus, having increased probabilities for mismatching properties P(BBB+−) and P(BBB−+)), is assigned a lower weight. In the example of predicting BBB crossing properties, the fingerprint weight may thus include the posterior probabilities P(BBB+|reference molecules BBB+, d) and P(BBB−|reference molecules BBB−, d). In other words, a fingerprint that is likely to correctly predict a BBB crossing property, given a distance, d, is assigned a high weight, whereas a fingerprint that is unlikely to correctly predict the BBB crossing property, given the distance, d is assigned a low weight.

Fingerprints weights may, thus, be obtained for all available fingerprints. A fingerprint weight may be, for example, in a numerical range of 0.0 . . . 1.0. While the optimization of fingerprint weights is illustrated based on the example of BBB crossing properties, those skilled in the art will appreciate that fingerprint weights may be obtained for any other molecule property.

The execution of Step 204 is optional, i.e., alternatively the subsequent steps may be performed using uniform weighting for the different types of fingerprints.

In Step 206, for each reference molecule, and using each of the fingerprints, distances to the sample molecule are calculated. The obtained distance between a reference molecule and the sample molecule may represent the inverse of the similarity of these two molecules, based on the type of fingerprint that was used for the calculation. In other words, shorter distances are obtained for more similar molecules, and longer distances are obtained for less similar molecules. In one embodiment of the invention, the Tanimoto distance is used. The distance calculations may be performed separately for each type of fingerprint. Accordingly, if ten types of fingerprints are available for a reference molecule and the sample molecule, ten distances are obtained to describe the similarity of the reference molecule and the sample molecule. Further, if a total of 50 reference molecules are available, a total of 500 distances (50×10) are obtained. The obtained distances describe the similarity of the reference molecules and the sample molecule in a high-dimensional space. The dimensionality of the space may be a result of the number of fingerprint types that are used. Specifically, in the above example, a ten-dimensional space (based on the use of 10 fingerprint types) may result, in which the 50 reference molecules are represented. Because each type of fingerprint characterizes the associated molecules in a slightly different way, the resulting distances may fluctuate between fingerprint types.

Figure 3B:
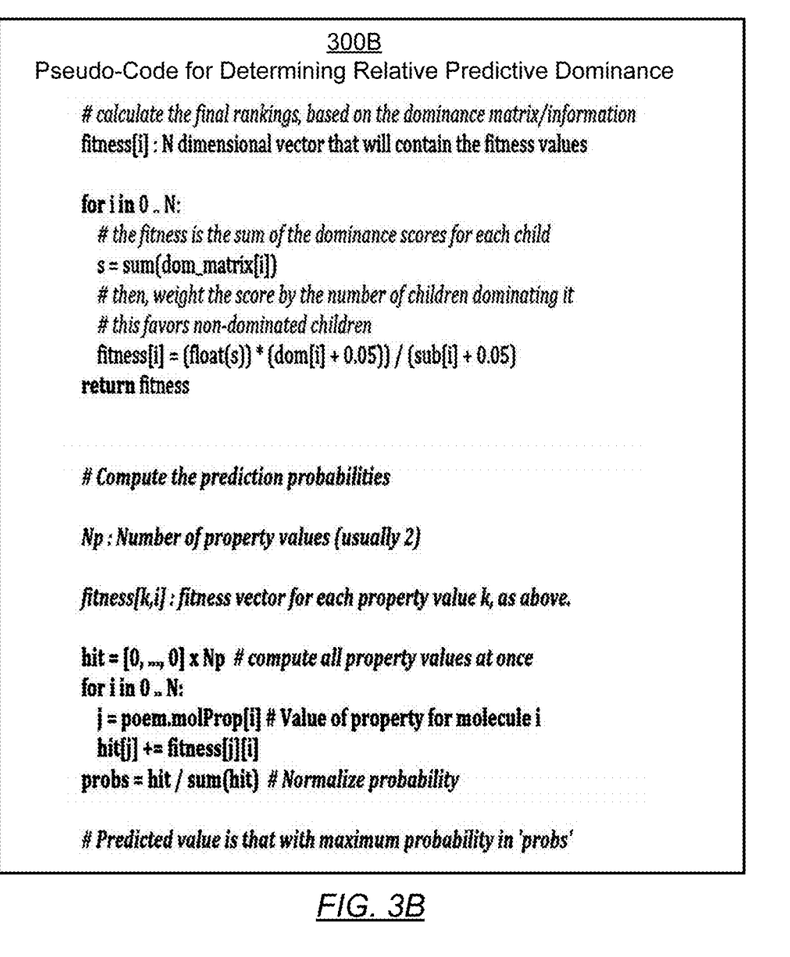

In Step 208, a relative predictive dominance is determined for each of the reference molecules. Specifically, each reference molecule may be compared to any other reference molecule, based on the distances obtained in Step 206. Consider, for example, reference molecules A and B, both associated with three fingerprints. Accordingly, after the execution of Step 206, three distances are available for each of the reference molecules A and B. Assume that the distances for molecule A are [0.6 0.4 0.7] and the distances for molecule B are [0.7 0.4 0.1]. In a direct comparison A vs B, for the first fingerprint, molecule A is closer than molecule B, for the second fingerprint, molecules A and B are equally close, and for the third fingerprint, molecule B is closer than molecule A. This may be documented in a scoring vector AvsB=[1 0.5 0], with "1" indicating that molecule A is closer than molecule B, 0 indicating that molecule B is closer than molecule A, and 0.5 indicating that molecules A and B are equally close. The weights obtained in Step 204 may be used to adjust the region in which distances are considered similar (resulting in a score of 0.5). A high weight may result in a narrow range in which distances would be considered similar, whereas a low weight may result in a broad range in which distances would be considered similar. A zero-weight would always result in a score of 0.5, regardless of the actual distances. The step may be performed for any combination of reference molecules. Pseudo-code that provides an example for an implementation is provided in FIG. 3A.

The predictive dominance for multiple reference molecules may be summarized in a dominance matrix that contains the predictive dominance values for the reference molecules.

In Step 210, fitness is determined for each reference molecule. In one or more embodiments of the invention, a scoring function is used to convert the dominance relationships, obtained in Step 208, into one single fitness value for each reference molecule. The fitness value may quantify how similar a particular reference molecule is to the sample molecule. The obtaining of a fitness for each of the reference molecules is illustrated by the pseudo-code provided in FIG. 3B. The scoring function, when assigning fitness values, may favor reference molecules that compare favorably on average, i.e., for all or the majority of fingerprints. These may be reference molecules that mostly "dominate" over other reference molecules (based on the predictive dominances obtained in Step 208) and that are less "dominated" by other reference molecules. In other words, a "best-of-class" reference molecule may be the reference molecule that for more fingerprints than any other reference molecule is closest to the target molecule.

In Step 212, the property of the sample molecule is predicted based on the properties of the reference molecules, scaled by the fitness values. The fitness values may be scaled to a numerical range of 0 . . . 1. In one embodiment of the invention, the fitness values are scaled such that the sum of all fitness values is "1". A "0" value, indicating a low (or no) fitness would suggest that the associated reference molecule is a poor candidate for predicting the property of the sample molecule. In contrast, a high value would indicate that the associated reference molecule is a highly suitable candidate to be used for predicting the property of the sample molecule. Accordingly, based on the fitness values associated with the reference molecules, the properties of the reference molecules may be considered for the prediction of the property of the sample molecule.

Consider, for example, a scenario in which a binary property is to be predicted for the sample molecule. "1" may be used to express that the property exists, and "0" may be used to express that the property does not exist. Assume that many reference molecules for which this property has previously been assessed are available. One of these reference molecules has the property, and the fitness value associated with this reference molecule was determined to be 0.78. Accordingly, in Step 212, this molecule would vote "1" with a contribution of 0.78. The same analysis may be performed for all other reference molecules to obtain a majority vote. Each of the reference molecules' contribution to the majority vote may be scaled based on the associated fitness values. Based on the majority vote, it is subsequently determined whether the binary property associated with the sample molecule is "0" or "1".

A similar prediction based on a majority vote may be made for properties that involve more than two classes. Further, a prediction of properties that are continuous may also be performed by scaling the contribution of each reference molecule based on the associated fitness values.

Various embodiments of the invention have one or more of the following advantages. Embodiments of the invention enable the prediction of properties of a sample molecule. The prediction considers multiple types of fingerprints, obtained for multiple reference molecules. Accordingly, no particular fingerprint needs to be selected prior to making a prediction. Distance-based metrics in a multi-dimensional space are used for the identification of molecular properties. No manual selection of hyper-parameters is necessary, and new reference molecules may be immediately considered in a prediction, as they become available. Based on the consideration of multiple fingerprints in a prediction, the risk of predictive bias and overfitting is reduced. The pitfalls of high-dimensional information are, thus, avoided.

Figure 4:
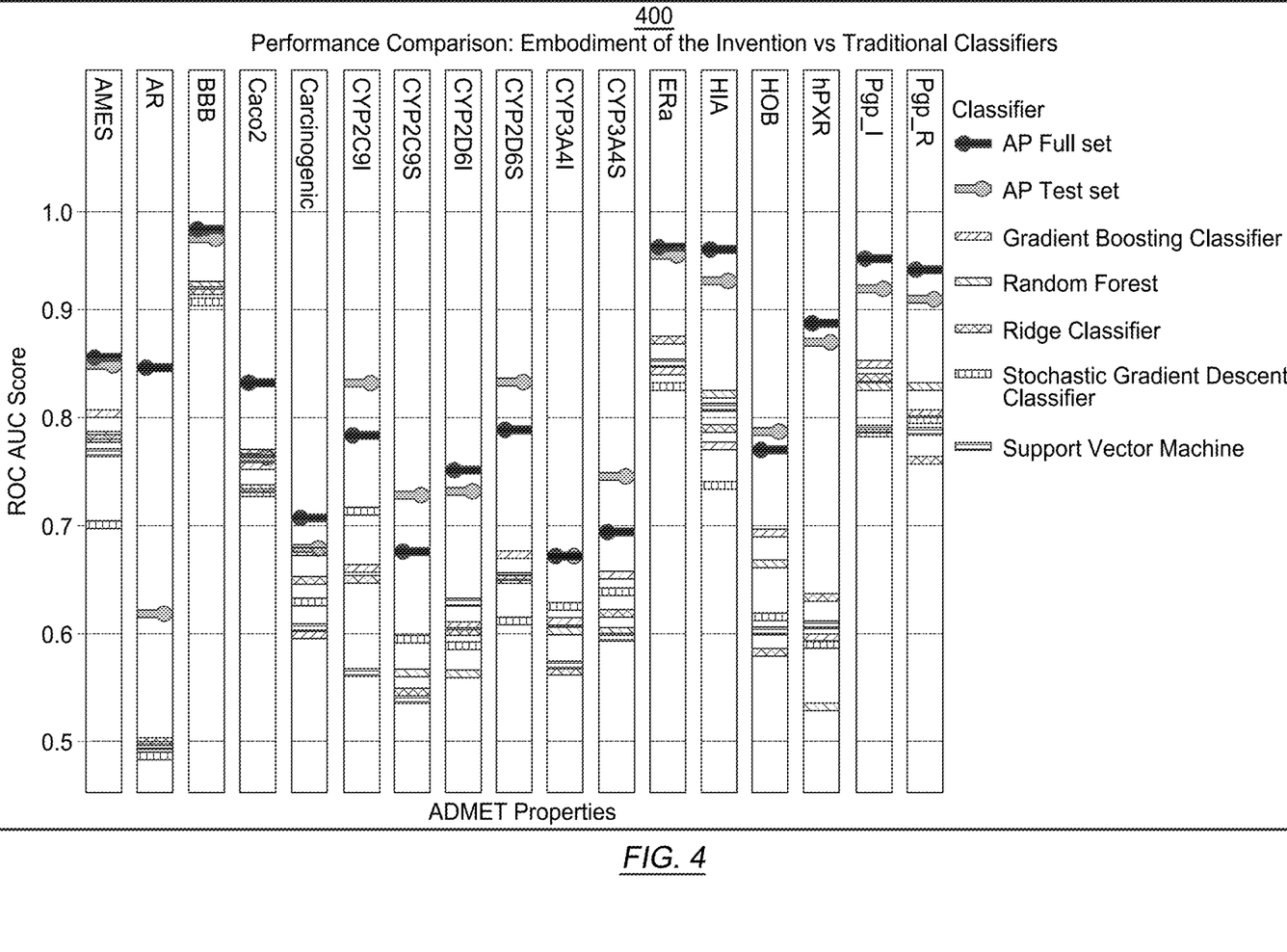
FIG. 4 shows a performance comparison of an embodiment of the invention and traditional classifiers.

FIG. 4 shows a performance comparison (400) of an embodiment of the invention and traditional classifiers. In the comparison, the embodiment was tested alongside five other traditional classifiers to predict 17 ADMET properties. For each of the five traditional approaches, a five-fold cross-validation using 80% of the dataset, leaving 20% for blind testing was performed. The process iterated through eight types of chemical fingerprints, and tuned hyperparameters using a grid-search strategy. For the embodiment of the invention the 80%/20% testing split was also applied for direct comparison (labeled "AP Test set"), as well as 'leave-one-out' full cross-validation (labeled "AP Full set") to assess predictive stability relative to the dataset size. Ten different fingerprints were simultaneously used to build one model, compared with only one fingerprint per traditional model in the standard approach. In the tests of the traditional classifiers, models were separately built for each fingerprint, and the one performing best in cross-validation scores was selected, and then the performance was measured on the test set. The predictive power for all models was assessed using the area under the Receiver Operator Characteristic curve (ROC AUC) measure of prediction performance. The datasets used for the 17 different models were obtained from curated, previously published QSAR studies, each focused on building an optimized model for a particular ADMET property.

As shown in FIG. 4, the embodiment of the invention consistently outperforms the five traditional classifiers for all 17 ADMET properties, based on the ROC AUC scores. Because embodiments of the invention have the ability to use all the data for training without the need for the 80/20% split needed with the traditional approaches, higher predictive power is obtained for most properties as shown by the difference between "AP Full" and "AP Test" in FIG. 4. Furthermore, even when using the same 80/20% data split that enables direct comparison of the embodiment of the invention and traditional classifiers, "AP Test" still outperforms each of the traditional classifiers.

Figure 5A:
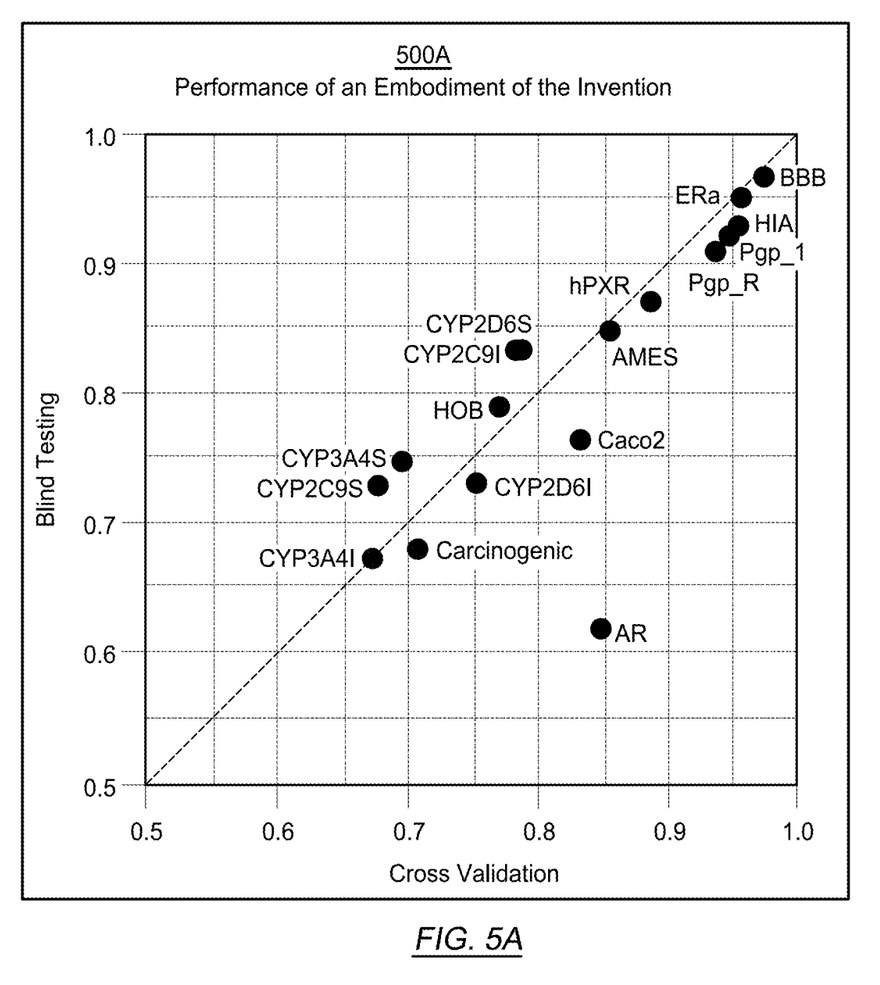
FIG. 5A shows cross validation versus blind testing ROC AUC scores for an embodiment of the invention.
Figure 5B:
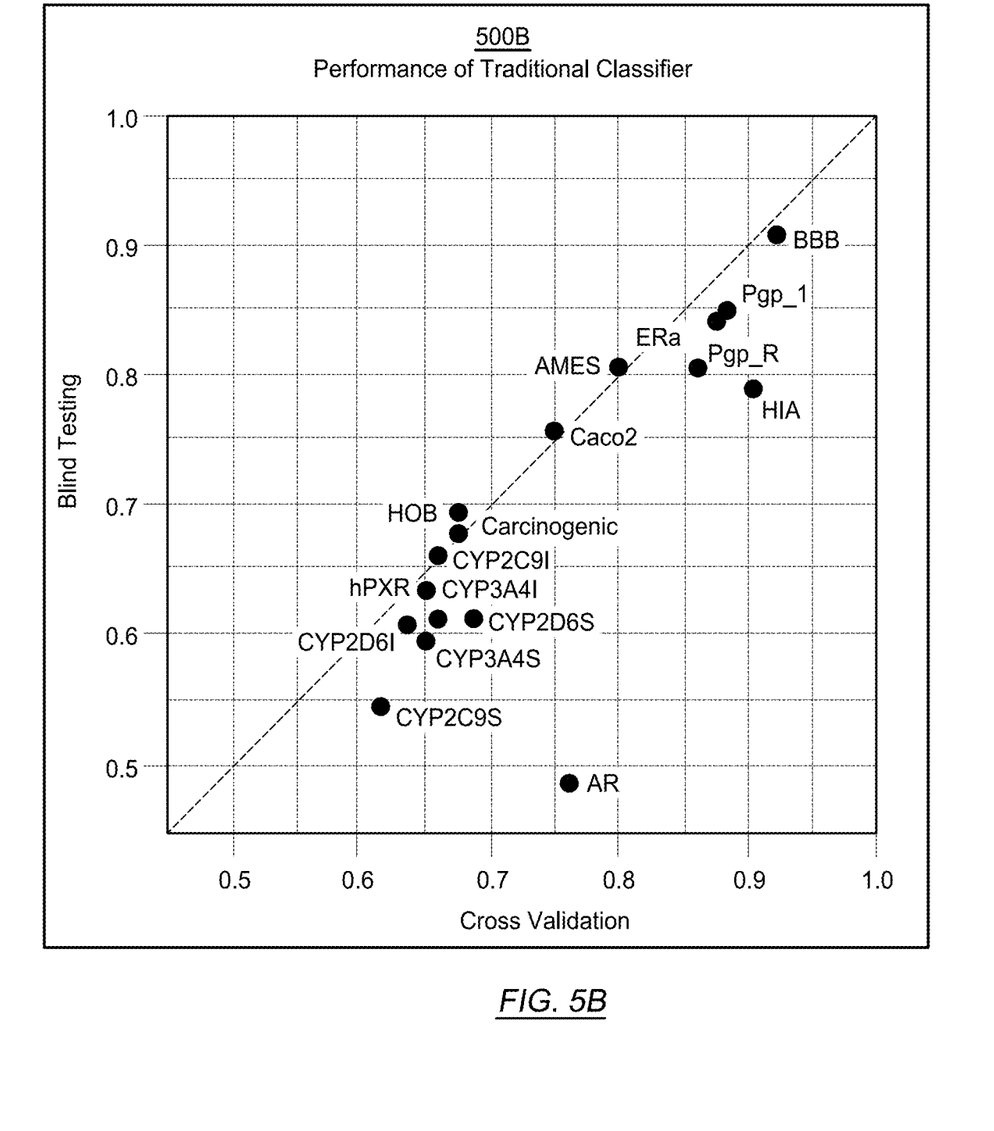
FIG. 5B show cross validation versus blind testing ROC AUC scores for a traditional Quantitative Structure-Activity Relationship (QSAR) approach.

FIG. 5A and FIG. 5B show cross validation versus blind testing ROC AUC scores for the embodiment of the invention (500A, FIG. 5A) and traditional Quantitative Structure-Activity Relationship (QSAR) approach (500B, FIG. 5B) to assess overfitting. Almost all properties represented by the different points in the plot of FIG. 5A (embodiment of the invention) fall on or very close on the diagonal line, versus FIG. 5B (traditional classifiers) where validation performance tends to be higher than test performance, indicating overfitting. Androgen Receptor (AR) binding models appear to overfit with both tools; however, the embodiment of the invention still performs better (Test: 0.62) than the best traditional classifier (Test: 0.50).

Figure 6:
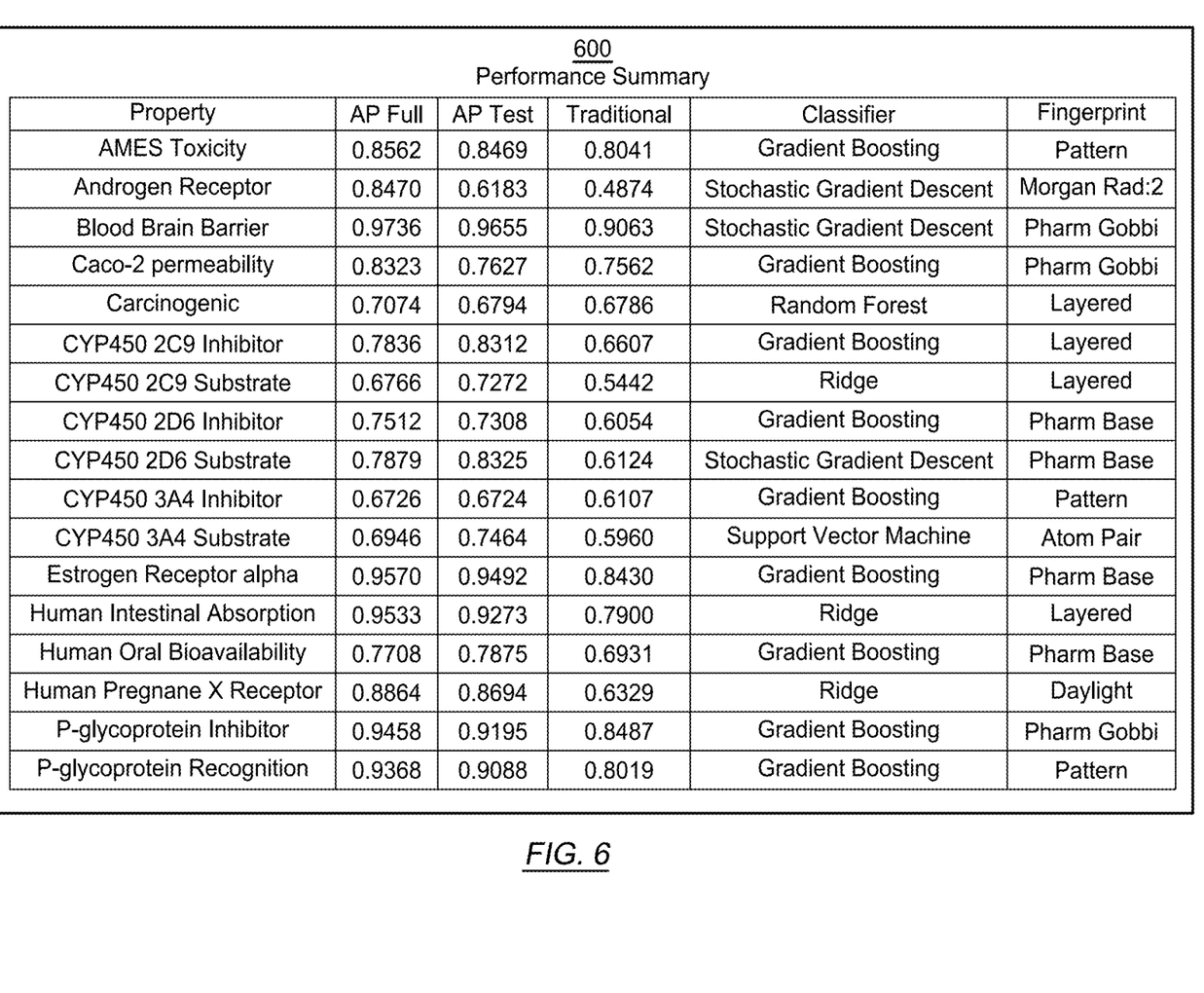
FIG. 6 shows a performance summary of an embodiment of the invention versus a best-performing traditional classifier-fingerprint combination.

FIG. 6 shows a performance summary (600) of an embodiment of the invention vs a best-performing traditional classifier-fingerprint combination. The inability of traditional classifiers to use many fingerprints at the same time leads to inconsistency in the type of fingerprints/classifiers generating the best performing models. This inconsistency is clearly apparent in Cytochrome P450 isoforms where for each isoform, a different fingerprint/classifier outputs the best performing classifier.

To address concerns related to the implementation of traditional classifiers, the performance of an embodiment of the invention was also compared with previously reported results in the literature. For example, Shen et al. (Shen J., et al. Estimation of ADME Properties with Substructure Pattern Recognition. J. Chem. Inf Model. 50, 1034-1041 (2010)) report on AdmetSAR, a tool used by DrugBank and assessed for performance on Blood Brain Barrier (BBB) and Human Intestinal Absorption (HIA) properties. Based on their report AdmetSAR ROC AUC scores (BBB: 0.9517, HIA: 0.9458) are outperformed by the embodiments of the invention (BBB: 0.9738, HIA: 0.9533).

In conclusion, embodiments of the invention consistently outperform conventional machine learning methods.

The prediction may be performed for a broad range of molecules to predict a broad range of properties. One or more embodiments of the invention may be particularly beneficial for the development of new drugs. Developing a drug is a long, expensive process. The ability to predict ADMET properties, using embodiments of the invention, may accelerate this process and may reduce cost. Further, because no hyperparameters need to optimized, unlike in typical machine learning-based methods, embodiments of the invention can be used by drug developers without a machine learning background.

Unlike traditional modelling approaches that provide highly specific tools designed to solve a single problem, embodiments of the invention are applicable to various disciplines beyond drug development. Any domain in which a quantitative or qualitative property for a molecule, interactions of molecules, etc. is to be predicted may benefit. Embodiments of the invention may be used wherever properties of a molecule are to be predicted; in a detection/development cycle of a new molecule to iteratively obtain a molecule with desired properties; and/or to identify alternative applications for existing molecules.

Figure 7A:
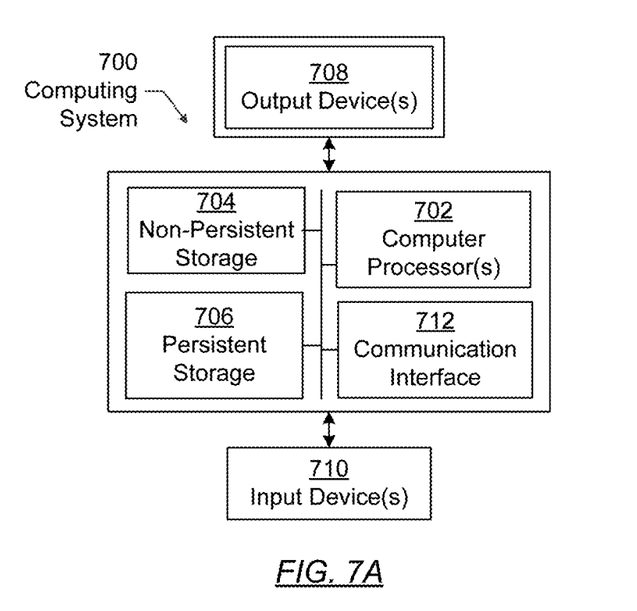
FIG. 7A and FIG. 7B shows computing systems, in accordance with one or more embodiments of the invention.

Embodiments of the disclosure may be implemented on a computing system. Any combination of mobile, desktop, server, router, switch, embedded device, or other types of hardware may be used. For example, as shown in FIG. 7A, the computing system (700) may include one or more computer processors (702), non-persistent storage (704) (e.g., volatile memory, such as random access memory (RAM), cache memory), persistent storage (706) (e.g., a hard disk, an optical drive such as a compact disk (CD) drive or digital versatile disk (DVD) drive, a flash memory, etc.), a communication interface (712) (e.g., Bluetooth interface, infrared interface, network interface, optical interface, etc.), and numerous other elements and functionalities.

The computer processor(s) (702) may be an integrated circuit for processing instructions. For example, the computer processor(s) may be one or more cores or micro-cores of a processor. The computing system (700) may also include one or more input devices (710), such as a touchscreen, keyboard, mouse, microphone, touchpad, electronic pen, or any other type of input device.

The communication interface (712) may include an integrated circuit for connecting the computing system (700) to a network (not shown) (e.g., a local area network (LAN), a wide area network (WAN) such as the Internet, mobile network, or any other type of network) and/or to another device, such as another computing device.

Further, the computing system (700) may include one or more output devices (708), such as a screen (e.g., a liquid crystal display (LCD), a plasma display, touchscreen, cathode ray tube (CRT) monitor, projector, or other display device), a printer, external storage, or any other output device. One or more of the output devices may be the same or different from the input device(s). The input and output device(s) may be locally or remotely connected to the computer processor(s) (702), non-persistent storage (704), and persistent storage (706). Many different types of computing systems exist, and the aforementioned input and output device(s) may take other forms.

Software instructions in the form of computer readable program code to perform embodiments of the disclosure may be stored, in whole or in part, temporarily or permanently, on a non-transitory computer readable medium such as a CD, DVD, storage device, a diskette, a tape, flash memory, physical memory, or any other computer readable storage medium. Specifically, the software instructions may correspond to computer readable program code that, when executed by a processor(s), is configured to perform one or more embodiments of the disclosure.

Figure 7B:
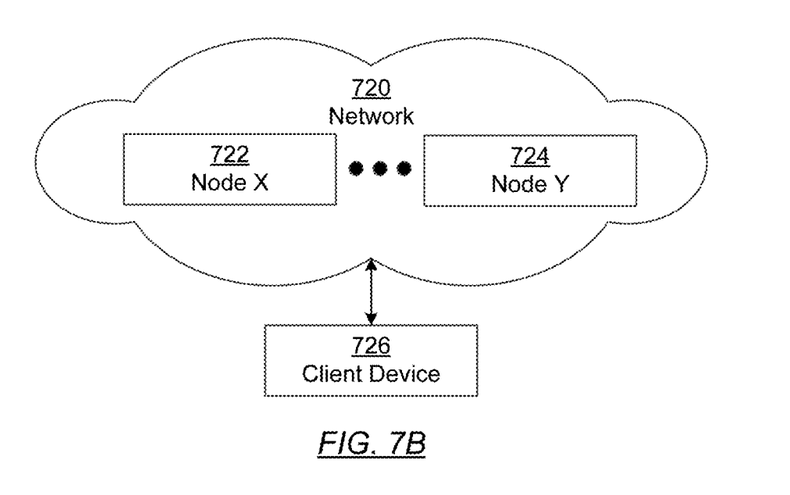

The computing system (700) in FIG. 7A may be connected to or be a part of a network. For example, as shown in FIG. 7B, the network (720) may include multiple nodes (e.g., node X (722), node Y (724)). Each node may correspond to a computing system, such as the computing system shown in FIG. 7A, or a group of nodes combined may correspond to the computing system shown in FIG. 7A. By way of an example, embodiments of the disclosure may be implemented on a node of a distributed system that is connected to other nodes. By way of another example, embodiments of the disclosure may be implemented on a distributed computing system having multiple nodes, where each portion of the disclosure may be located on a different node within the distributed computing system. Further, one or more elements of the aforementioned computing system (700) may be located at a remote location and connected to the other elements over a network.

Although not shown in FIG. 7B, the node may correspond to a blade in a server chassis that is connected to other nodes via a backplane. By way of another example, the node may correspond to a server in a data center. By way of another example, the node may correspond to a computer processor or micro-core of a computer processor with shared memory and/or resources.

The nodes (e.g., node X (722), node Y (724)) in the network (720) may be configured to provide services for a client device (726). For example, the nodes may be part of a cloud computing system. The nodes may include functionality to receive requests from the client device (726) and transmit responses to the client device (726). The client device (726) may be a computing system, such as the computing system shown in FIG. 7A. Further, the client device (726) may include and/or perform all or a portion of one or more embodiments of the disclosure.

The computing system or group of computing systems described in FIG. 7A and FIG. 7B may include functionality to perform a variety of operations disclosed herein. For example, the computing system(s) may perform communication between processes on the same or different system. A variety of mechanisms, employing some form of active or passive communication, may facilitate the exchange of data between processes on the same device. Examples representative of these inter-process communications include, but are not limited to, the implementation of a file, a signal, a socket, a message queue, a pipeline, a semaphore, shared memory, message passing, and a memory-mapped file. Further details pertaining to a couple of these non-limiting examples are provided below.

Based on the client-server networking model, sockets may serve as interfaces or communication channel endpoints enabling bidirectional data transfer between processes on the same device. Foremost, following the client-server networking model, a server process (e.g., a process that provides data) may create a first socket object. Next, the server process binds the first socket object, thereby associating the first socket object with a unique name and/or address. After creating and binding the first socket object, the server process then waits and listens for incoming connection requests from one or more client processes (e.g., processes that seek data). At this point, when a client process wishes to obtain data from a server process, the client process starts by creating a second socket object. The client process then proceeds to generate a connection request that includes at least the second socket object and the unique name and/or address associated with the first socket object. The client process then transmits the connection request to the server process. Depending on availability, the server process may accept the connection request, establishing a communication channel with the client process, or the server process, busy in handling other operations, may queue the connection request in a buffer until server process is ready. An established connection informs the client process that communications may commence. In response, the client process may generate a data request specifying the data that the client process wishes to obtain. The data request is subsequently transmitted to the server process. Upon receiving the data request, the server process analyzes the request and gathers the requested data. Finally, the server process then generates a reply including at least the requested data and transmits the reply to the client process. The data may be transferred, more commonly, as datagrams or a stream of characters (e.g., bytes).

Shared memory refers to the allocation of virtual memory space in order to substantiate a mechanism for which data may be communicated and/or accessed by multiple processes. In implementing shared memory, an initializing process first creates a shareable segment in persistent or non-persistent storage. Post creation, the initializing process then mounts the shareable segment, subsequently mapping the shareable segment into the address space associated with the initializing process. Following the mounting, the initializing process proceeds to identify and grant access permission to one or more authorized processes that may also write and read data to and from the shareable segment. Changes made to the data in the shareable segment by one process may immediately affect other processes, which are also linked to the shareable segment. Further, when one of the authorized processes accesses the shareable segment, the shareable segment maps to the address space of that authorized process. Often, only one authorized process may mount the shareable segment, other than the initializing process, at any given time.

Other techniques may be used to share data, such as the various data described in the present application, between processes without departing from the scope of the disclosure. The processes may be part of the same or different application and may execute on the same or different computing system.

Rather than or in addition to sharing data between processes, the computing system performing one or more embodiments of the disclosure may include functionality to receive data from a user. For example, in one or more embodiments, a user may submit data via a graphical user interface (GUI) on the user device. Data may be submitted via the graphical user interface by a user selecting one or more graphical user interface widgets or inserting text and other data into graphical user interface widgets using a touchpad, a keyboard, a mouse, or any other input device. In response to selecting a particular item, information regarding the particular item may be obtained from persistent or non-persistent storage by the computer processor. Upon selection of the item by the user, the contents of the obtained data regarding the particular item may be displayed on the user device in response to the user's selection.

By way of another example, a request to obtain data regarding the particular item may be sent to a server operatively connected to the user device through a network. For example, the user may select a uniform resource locator (URL) link within a web client of the user device, thereby initiating a Hypertext Transfer Protocol (HTTP) or other protocol request being sent to the network host associated with the URL. In response to the request, the server may extract the data regarding the particular selected item and send the data to the device that initiated the request. Once the user device has received the data regarding the particular item, the contents of the received data regarding the particular item may be displayed on the user device in response to the user's selection. Further to the above example, the data received from the server after selecting the URL link may provide a web page in Hyper Text Markup Language (HTML) that may be rendered by the web client and displayed on the user device.

Once data is obtained, such as by using techniques described above or from storage, the computing system, in performing one or more embodiments of the disclosure, may extract one or more data items from the obtained data. For example, the extraction may be performed as follows by the computing system in FIG. 7A. First, the organizing pattern (e.g., grammar, schema, layout) of the data is determined, which may be based on one or more of the following: position (e.g., bit or column position, Nth token in a data stream, etc.), attribute (where the attribute is associated with one or more values), or a hierarchical/tree structure (consisting of layers of nodes at different levels of detail-such as in nested packet headers or nested document sections). Then, the raw, unprocessed stream of data symbols is parsed, in the context of the organizing pattern, into a stream (or layered structure) of tokens (where each token may have an associated token "type").

Next, extraction criteria are used to extract one or more data items from the token stream or structure, where the extraction criteria are processed according to the organizing pattern to extract one or more tokens (or nodes from a layered structure). For position-based data, the token(s) at the position(s) identified by the extraction criteria are extracted. For attribute/value-based data, the token(s) and/or node(s) associated with the attribute(s) satisfying the extraction criteria are extracted. For hierarchical/layered data, the token(s) associated with the node(s) matching the extraction criteria are extracted. The extraction criteria may be as simple as an identifier string or may be a query provided to a structured data repository (where the data repository may be organized according to a database schema or data format, such as XML).

The extracted data may be used for further processing by the computing system. For example, the computing system of FIG. 7A, while performing one or more embodiments of the disclosure, may perform data comparison. Data comparison may be used to compare two or more data values (e.g., A, B). For example, one or more embodiments may determine whether A>B, A=B, A!=B, A<B, etc. The comparison may be performed by submitting A, B, and an opcode specifying an operation related to the comparison into an arithmetic logic unit (ALU) (i.e., circuitry that performs arithmetic and/or bitwise logical operations on the two data values). The ALU outputs the numerical result of the operation and/or one or more status flags related to the numerical result. For example, the status flags may indicate whether the numerical result is a positive number, a negative number, zero, etc. By selecting the proper opcode and then reading the numerical results and/or status flags, the comparison may be executed. For example, in order to determine if A>B, B may be subtracted from A (i.e., A−B), and the status flags may be read to determine if the result is positive (i.e., if A>B, then A−B>0). In one or more embodiments, B may be considered a threshold, and A is deemed to satisfy the threshold if A=B or if A>B, as determined using the ALU. In one or more embodiments of the disclosure, A and B may be vectors, and comparing A with B requires comparing the first element of vector A with the first element of vector B, the second element of vector A with the second element of vector B, etc. In one or more embodiments, if A and B are strings, the binary values of the strings may be compared.

The computing system in FIG. 7A may implement and/or be connected to a data repository. For example, one type of data repository is a database. A database is a collection of information configured for ease of data retrieval, modification, re-organization, and deletion. Database Management System (DBMS) is a software application that provides an interface for users to define, create, query, update, or administer databases.

The user, or software application, may submit a statement or query into the DBMS. Then the DBMS interprets the statement. The statement may be a select statement to request information, update statement, create statement, delete statement, etc. Moreover, the statement may include parameters that specify data, or data container (database, table, record, column, view, etc.), identifier(s), conditions (comparison operators), functions (e.g. join, full join, count, average, etc.), sort (e.g. ascending, descending), or others. The DBMS may execute the statement. For example, the DBMS may access a memory buffer, a reference or index a file for read, write, deletion, or any combination thereof, for responding to the statement. The DBMS may load the data from persistent or non-persistent storage and perform computations to respond to the query. The DBMS may return the result(s) to the user or software application.

The computing system of FIG. 7A may include functionality to provide raw and/or processed data, such as results of comparisons and other processing. For example, providing data may be accomplished through various presenting methods. Specifically, data may be provided through a user interface provided by a computing device. The user interface may include a GUI that displays information on a display device, such as a computer monitor or a touchscreen on a handheld computer device. The GUI may include various GUI widgets that organize what data is shown as well as how data is provided to a user. Furthermore, the GUI may provide data directly to the user, e.g., data provided as actual data values through text, or rendered by the computing device into a visual representation of the data, such as through visualizing a data model.

For example, a GUI may first obtain a notification from a software application requesting that a particular data object be provided within the GUI. Next, the GUI may determine a data object type associated with the particular data object, e.g., by obtaining data from a data attribute within the data object that identifies the data object type. Then, the GUI may determine any rules designated for displaying that data object type, e.g., rules specified by a software framework for a data object class or according to any local parameters defined by the GUI for presenting that data object type. Finally, the GUI may obtain data values from the particular data object and render a visual representation of the data values within a display device according to the designated rules for that data object type.

Data may also be provided through various audio methods. In particular, data may be rendered into an audio format and provided as sound through one or more speakers operably connected to a computing device.

Data may also be provided to a user through haptic methods. For example, haptic methods may include vibrations or other physical signals generated by the computing system. For example, data may be provided to a user using a vibration generated by a handheld computer device with a predefined duration and intensity of the vibration to communicate the data.

The above description of functions presents only a few examples of functions performed by the computing system of FIG. 7A and the nodes and/or client device in FIG. 7B. Other functions may be performed using one or more embodiments of the disclosure.

While the disclosure has been described with respect to a limited number of embodiments, those skilled in the art, having benefit of this disclosure, will appreciate that other embodiments can be devised which do not depart from the scope of the disclosure as disclosed herein. Accordingly, the scope of the disclosure should be limited only by the attached claims.

The embodiments and examples set forth herein were presented in order to best explain the present invention and its particular application and to thereby enable those skilled in the art to make and use the invention. However, those skilled in the art will recognize that the foregoing description and examples have been presented for the purposes of illustration and example only. The description as set forth is not intended to be exhaustive or to limit the invention to the precise form disclosed.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A computer-implemented method for predicting a property of a sample molecule, the computer-implemented method comprising:
   for each of a plurality of reference molecules, obtaining a plurality of fingerprints and at least one property;
   obtaining the plurality of fingerprints of the sample molecule;
   for each of the plurality of reference molecules, using each of the plurality of fingerprints, calculating distances to the sample molecule in a multi-dimensional feature space wherein a dimensionality of the multi-dimensional feature space corresponds to a number of the plurality of fingerprints;
   for each of the plurality of reference molecules, determining a relative predictive dominance, based on the distances to the sample molecule, wherein determining the relative predictive dominance comprises obtaining a scoring vector by comparing a first distance between a first reference molecule of the plurality of reference molecules and the sample molecule and a second distance between a second reference molecule of the plurality of reference molecules and the sample molecule within the multi-dimensional feature space;
   for each of the plurality of reference molecules, determining an associated fitness value based on the relative predictive dominance wherein the associated fitness value quantifies a measure of similarity between each of the plurality of reference molecules relative to the sample molecule; and
   predicting the at least one property of the sample molecule based on the at least one property of each of the plurality of reference molecules and the associated fitness value for each of the plurality of reference molecules by obtaining a majority vote on the at least one property by each of the plurality of reference molecules and scaling a contribution by each of the plurality of reference molecules to the majority vote by the associated fitness value.

2. The computer-implemented method of claim 1, wherein calculating distances to the sample molecule comprises:
   for each of the plurality of reference molecules, computing a Tanimoto distance to the sample molecule.

3. The computer-implemented method of claim 1, wherein determining the relative predictive dominance comprises:
   obtaining an additional scoring vector by comparing a third distance between a third reference molecule of the plurality of reference molecules and the sample molecule and the first distance between the first reference molecule of the plurality of reference molecules.

4. The computer-implemented method of claim 1, wherein the scoring vector indicates whether the first reference molecule or the second reference molecule is closer to the sample molecule.

5. The computer-implemented method of claim 3, wherein determining the relative predictive dominance further comprises:
   combining the scoring vector with the additional scoring vector to form a dominance matrix.

6. The computer-implemented method of claim 1, wherein determining the associated fitness value based on the relative predictive dominance comprises:

favoring one reference molecule over other reference molecules of the plurality of reference molecules based on the one reference molecule being closer to the sample molecule for more fingerprints of the plurality of fingerprints than any of the other reference molecules.

7. The computer-implemented method of claim 1, where the at least one property is at least one selected from:
   a binary property, and
   a continuous property.

8. A system for predicting a property of a sample molecule, the system comprising:
   a reference molecule repository; and
   a molecule property prediction engine configured to:
      for each of a plurality of reference molecules, obtaining a plurality of fingerprints and at least one property from the reference molecule repository;
      obtaining the plurality of fingerprints of the sample molecule;
      for each of the plurality of reference molecules, using each of the plurality of fingerprints, calculating distances to the sample molecule in a multi-dimensional feature space wherein a dimensionality of the multi-dimensional feature space corresponds to a number of the plurality of fingerprints;
      for each of the plurality of reference molecules, determining a relative predictive dominance, based on the distances to the sample molecule, wherein determining the relative predictive dominance comprises obtaining a scoring vector by comparing a first distance between a first reference molecule of the plurality of reference molecules and the sample molecule and a second distance between a second reference molecule of the plurality of reference molecules and the sample molecule within the multi-dimensional feature space;
      for each of the plurality of reference molecules, determining an associated fitness value based on the relative predictive dominance wherein the associated fitness value quantifies a measure of similarity between each of the plurality of reference molecules relative to the sample molecule; and
      predicting the at least one property of the sample molecule based on the at least one property of each of the plurality of reference molecules and the associated fitness value for each of the plurality of reference molecules by obtaining a majority vote on the at least one property by each of the plurality of reference molecules and scaling a contribution by each of the plurality of reference molecules to the majority vote by the associated fitness value.

9. The system of claim 8, wherein determining the relative predictive dominance comprises:
   obtaining an additional scoring vector by comparing a third distance between a third reference molecule of the plurality of reference molecules and the sample molecule and the first distance between the first reference molecule of the plurality of reference molecules, wherein the additional scoring vector indicates, whether the first reference molecule or the third reference molecule is closer to the sample molecule.

10. The system of claim 8, wherein determining the associated fitness value based on the relative predictive dominance comprises:
   favoring one reference molecule over other reference molecules of the plurality of reference molecules based on the one reference molecule being closer to the sample molecule for more fingerprints of the plurality of fingerprints than any of the other reference molecules.

11. A non-transitory computer readable medium comprising computer readable program code for predicting a property of a sample molecule, the computer readable program code causing a computer system to:
   for each of a plurality of reference molecules, obtaining a plurality of fingerprints and at least one property;
   obtaining the plurality of fingerprints of the sample molecule;
   for each of the plurality of reference molecules, using each of the plurality of fingerprints, calculating distances to the sample molecule in a multi-dimensional feature space wherein a dimensionality of the multi-dimensional feature space corresponds to a number of the plurality of fingerprints;
   for each of the plurality of reference molecules, determining a relative predictive dominance, based on the distances to the sample molecule, wherein determining the relative predictive dominance comprises obtaining a scoring vector by comparing a first distance between a first reference molecule of the plurality of reference molecules and the sample molecule and a second distance between a second reference molecule of the plurality of reference molecules and the sample molecule within the multi-dimensional feature space;
   for each of the plurality of reference molecules, determining an associated fitness value based on the relative predictive dominance wherein the associated fitness value quantifies a measure of similarity between each of the plurality of reference molecules relative to the sample molecule; and
   predicting the at least one property of the sample molecule based on the at least one property of each of the plurality of reference molecules and the associated fitness value for each of the plurality of reference molecules by obtaining a majority vote on the at least one property by each of the plurality of reference molecules and scaling a contribution by each of the plurality of reference molecules to the majority vote by the associated fitness value.

12. The non-transitory computer readable medium of claim 11, wherein determining the relative predictive dominance comprises:
   obtaining an additional scoring vector by comparing a third distance between a third reference molecule of the plurality of reference molecules and the sample molecule and the first distance between the first reference molecule of the plurality of reference molecules.

13. The non-transitory computer readable medium of claim 12,
   wherein the scoring vector indicates whether the first reference molecule or the second reference molecule is closer to the sample molecule.

14. The non-transitory computer readable medium of claim 12, wherein determining the relative predictive dominance further comprises:
   combining the scoring vector with the additional scoring vector to form a dominance matrix.

15. The non-transitory computer readable medium of claim 11, wherein determining the associated fitness value based on the relative predictive dominance comprises:
   favoring one reference molecule over other reference molecules of the plurality of reference molecules based on the one reference molecule being closer to the sample molecule for more fingerprints of the plurality of fingerprints than any of the other reference molecules.

16. The non-transitory computer readable medium of claim 11, where the at least one property is at least one selected from:
a binary property, and a continuous property.

\* \* \* \* \*